(12) United States Patent
Muuranto et al.

(10) Patent No.: US 11,298,087 B2
(45) Date of Patent: Apr. 12, 2022

(54) METHOD AND SYSTEM FOR PREDICTING PHYSIOLOGICAL ALARM FREQUENCY BY PATIENT MONITORS

(71) Applicant: GE Precision Healthcare LLC, Wauwatosa, WI (US)

(72) Inventors: Erno Petteri Muuranto, Helsinki (FI); Kimmo Henrik Uutela, Helsinki (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 208 days.

(21) Appl. No.: 16/690,585

(22) Filed: Nov. 21, 2019

(65) Prior Publication Data

US 2021/0153815 A1    May 27, 2021

(51) Int. Cl.
*G16H 40/20* (2018.01)
*G16H 50/30* (2018.01)
*A61B 5/00* (2006.01)

(52) U.S. Cl.
CPC .............. *A61B 5/746* (2013.01); *A61B 5/002* (2013.01); *A61B 5/7275* (2013.01); *G16H 40/20* (2018.01); *G16H 50/30* (2018.01)

(58) Field of Classification Search
CPC ....... A61B 5/746; A61B 5/7275; A61B 5/002; G16H 40/20; G16H 50/30
See application file for complete search history.

(56) References Cited

U.S. PATENT DOCUMENTS

| | | | |
|---|---|---|---|
| 10,255,994 B2 | 4/2019 | Sampath et al. | |
| 2013/0015966 A1 | 1/2013 | Soomro et al. | |
| 2015/0364022 A1* | 12/2015 | Dyell | G16H 40/63 340/573.1 |
| 2017/0000424 A1* | 1/2017 | Friedman | A61B 5/0816 |

(Continued)

OTHER PUBLICATIONS

Welch et al., Multi-parameter vital sign database to assist in alarm optimization for general care units, J. Clin. Monit Comput., 2016, pp. 895-900.

(Continued)

*Primary Examiner* — Brian T Gedeon
*Assistant Examiner* — Joshua Andrew Schum-Houck
(74) *Attorney, Agent, or Firm* — Andrus Intellectual Property Law, LLP

(57) ABSTRACT

A method of predicting physiological alarm frequency by patient monitors includes collecting patient monitoring data of multiple patients in at least a first healthcare environment, and then determining an alarm rate model based on the patient monitoring data, wherein the alarm rate model describes alarm rates at a range of alarm configurations in the first healthcare environment. Initial alarm rate data is collected for a second healthcare environment, wherein the initial alarm rate data includes at least one alarm rate at at least one known alarm configuration within the range of alarm configurations. An alarm rate transform is then calculated for the second healthcare environment comparing the initial alarm rate data for the second healthcare environment to the alarm rate model. Alarm rates are predicted for (Continued)

the second healthcare environment at a different alarm configuration than the at least one known alarm configuration of the initial alarm rate data by applying the alarm rate transform to the alarm rate model.

20 Claims, 4 Drawing Sheets

(56) References Cited

U.S. PATENT DOCUMENTS

2017/0061089 A1* 3/2017 De Waele .............. G16H 40/63
2018/0182484 A1* 6/2018 Sampath ................ G16H 40/67

OTHER PUBLICATIONS

Rheineck-Leyssius et al., Influence of pulse oximeter settings on the frequency of alarms and detection of hypoxemia: Theoretical effects of artifact rejection, alarm delay, averaging, median filtering or a lower setting of the alarm limit, J ClinMonit 1998; 14: pp. 151-156.

* cited by examiner

|  | Alarm delay | | | | |
|---|---|---|---|---|---|
|  | 0s | 15s | 30s | 60s | 90s |
| 50 | 31.7 | 15.8 | 8.3 | 2.6 | 1.4 |
| 48 | 15.4 | 7.7 | 4.1 | 1.0 | 0.4 |
| 46 | 6.9 | 3.5 | 1.6 | 0.6 | 0.4 |
| 44 | 4.5 | 2.2 | 1.6 | 0.6 | 0.4 |
| 42 | 3.7 | 1.8 | 1.2 | 0.6 | 0.4 |
| 40 | 2.8 | 1.4 | 1.0 | 0.2 | 0.2 |

(Alarm limit, rows; label 50)

FIG. 2A

|  | Alarm delay | | | | |
|---|---|---|---|---|---|
|  | 0s | 15s | 30s | 60s | 90s |
| 50 | 31.7/3m | 15.8/2.7m | 8.3/2.4 | 2.6/2.0 | 1.4/1.4 |
| 48 | 15.4/2.4m | 7.7/2.1m | 4.1/1.7m | -/- | -/- |
| 46 | -/- | 3.5/1.6 | 1.6/1.1 | -/- | -/- |
| 44 | -/- | 2.2/1.0 | -/- | -/- | -/- |
| 42 | -/- | -/- | -/- | -/- | -/- |
| 40 | -/- | -/- | -/- | -/- | 0.2/0.2m |

(Alarm limit, rows; label 50)

FIG. 2B

| Alarm limit | Alarm delay | | | | |
|---|---|---|---|---|---|
| | 0s | 15s | 30s | 60s | 90s |
| 50 | | | | | |
| 48 | | | | | |
| 46 | | | 1.5/1.6m | | |
| 44 | | 2.0/1.5m | | | |
| 42 | | | | | |
| 40 | | | | | |

60

METHOD AND SYSTEM FOR PREDICTING PHYSIOLOGICAL ALARM FREQUENCY BY PATIENT MONITORS

BACKGROUND

The present disclosure generally relates to systems, devices, methods relating to physiological monitoring of patients in hospitals and other patient care facilities, and more particularly to systems, devices, and methods for predicting physiological alarm frequency by patient monitors.

Hospitals, nursing homes, outpatient centers, and other healthcare facilities typically include physiological patient monitoring devices at one or more bedsides in the facility. Patient monitoring devices generally include sensors, processing equipment, and displays for obtaining and analyzing a medical patient's physiological parameters. Physiological parameters include, for example, heart rate, ECG waveform parameters, respiratory rate, $SpO_2$ level, pulse, and blood pressure, among others. Clinicians, including doctors, nurses, and certain other medical personnel use the physiological parameters obtained from the medical patient to diagnose illnesses and to prescribe treatments. Clinicians also use the physiological parameters to monitor a patient during various clinical situations to determine whether to increase the level of medical care given to the patient.

These patient monitors all generate a variety of alarms, which range from routine to critical in the severity of the event indicated. Automated alarms can be beneficial to algorithmically determine when an event related to a patient monitoring device or a patient therapy device has occurred. These algorithms generally compare one or more parameters from the medical device to one or more predefined threshold settings, or otherwise conduct pattern matching or other waveform analysis to flag potential issues. Alarm algorithms may be threshold comparisons, but may also include logical combinations, including boolean logic, fuzzy logic, and/or pattern matching. These automated alarms can be beneficial to draw clinician attention to the detection and/or occurrence of an event. Additionally, each monitoring, treatment, and/or support device or system may generate alarms regarding a technical problem with the monitoring and/or care delivery device or setup, i.e., a technical alarm. These technical alarms may indicate any of various technical problems, such as disconnection of a sensor device from the patient or from a monitoring device, a low battery, or some other technical issue with the device itself or the connection to the patient.

While each alarm may indicate a condition or event of some importance or relevance, a significant number of alarms can be generated during routine care and these alarms place a burden both on patients who may be bothered (e.g., woken up or concerned) by alarm events as well as on clinicians who must divert time and attention from other care tasks or activities to attend to these alarms. A significant number of clinically irrelevant alarms can create alarm fatigue in clinicians whereby the attention to the large volume of alarms can slow recognition or response to alarms, including alarms indicating important or critical events.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a method of predicting physiological alarm frequency by patient monitors includes collecting patient monitoring data of multiple patients in at least a first healthcare environment, and then determining an alarm rate model based on the patient monitoring data, wherein the alarm rate model describes alarm rates at a range of alarm configurations in the first healthcare environment. Initial alarm rate data is collected for a second healthcare environment, wherein the initial alarm rate data includes at least one alarm rate at at least one known alarm configuration within the range of alarm configurations. An alarm rate transform is then calculated for the second healthcare environment comparing the initial alarm rate data for the second healthcare environment to the alarm rate model. Alarm rates are predicted for the second healthcare environment at a different alarm configuration than the at least one known alarm configuration of the initial alarm rate data by applying the alarm rate transform to the alarm rate model.

In one embodiment, a system for predicting physiological alarm frequency by patient monitors includes an alarm rate model stored on a memory, wherein the alarm rate model described alarm rates at a range of alarm configurations and is based on patient monitoring data from multiple patients in at least a first healthcare environment. A plurality of patient monitors is configured to collect patient monitoring data from patients in a second healthcare environment and a processor is configured to receive initial alarm rate data for a second healthcare environment that is based on the patient monitoring data collected therein. The initial alarm rate data includes at least one alarm rate at at least one known alarm configuration within the range of alarm configurations represented in the alarm rate model. An alarm rate transform is then calculation for the second healthcare environment comparing the initial alarm rate data for the second healthcare environment to the alarm rate model. Alarm rates can then be predicted for the second healthcare environment at a different alarm configuration than the at last one known alarm configuration of the initial alarm rate data based on the alarm rate transform.

In one embodiment, a non-transitory computer readable medium is configured for predicting physiological alarm frequency by patient monitors. The non-transitory computer readable medium contains program instructions that cause the computer to perform steps including receiving an alarm rate model based on patient monitoring data from the first environment and receiving initial alarm rate data based on patient monitoring data from a second healthcare environment. The alarm rate model describes alarm rates range of alarm configuration, and the initial alarm rate data includes at least one alarm rate at at least one known alarm configuration that is within the range of alarm configurations represented in the alarm rate model. Steps are then executed to compare the initial alarm rate data for the second healthcare environment to the alarm rate model, and then to calculate an alarm rate transform for the second healthcare environment based on the comparison. Alarm rates are then predicted for the second healthcare environment at different alarm configurations than the at least one known alarm configuration of the initial alarm rate data based on the alarm rate transform.

Various other features, objects, and advantages of the invention will be made apparent from the following description taken together with the drawings.

BRIEF DESCRIPTION OF THE DRAWINGS

The present disclosure is described with reference to the following Figures.

FIGS. 2A and 2B depict embodiments of model alarm rate data used to generate an alarm rate model.

DETAILED DESCRIPTION

Figure 1:
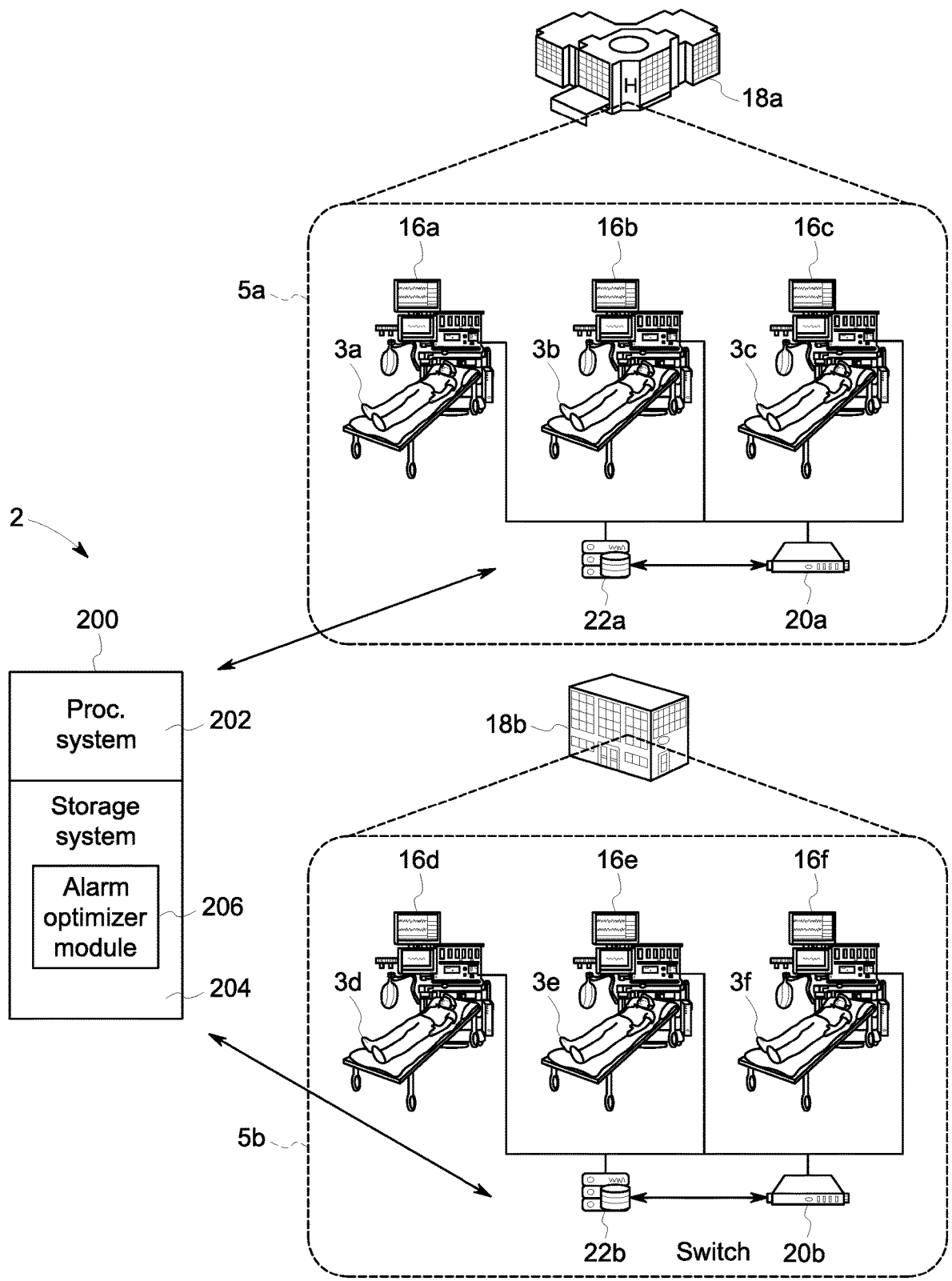
FIG. 1 schematically depicts a system for predicting physiological alarm frequency according to one embodiment of the disclosure.

Medical device alarms are helpful to draw clinician attention to alarms, which may regard technical issues with the patient monitoring arrangement or devices or a physiological event detected in the physiological data recorded from that patient. However, given the number of patient monitoring devices and other care devices that generate alarms, often simultaneously, alarm response can overburden and overwhelm clinicians and present a barrier to effectively managing and responding to alarms, some of which are for critical health-related emergencies. If too many alarms are initiated, clinicians are likely to suffer from alarm fatigue and, if auditory alarms are generated, patients hearing the alarms are likely to become agitated.

Accordingly, there is a need for an effective system and method that predicts physiological alarm frequency. The inventors have recognized that, to the extent that currently available systems and methods for assessing patient monitoring configurations in relation to alarms are available, they rely on large amounts of physiological parameter data collected with a sufficient rate, such as at least one sample per second, from each of multiple patients. In some embodiments, medical monitoring devices or system are capable of collecting large amounts of physiological parameter data from a number of patients, and using that data to simulate a variety of alarm condition detection criteria and/or alarm notification delay times that can be analyzed and used to alter actual alarm condition detection criteria and/or alarm notification delay times.

The inventors have recognized that acquisition of such full numeric data is expensive and time consuming, and thus such full numeric data is often not available. Certain methods and systems have utilized alarm event data, rather than full numeric data, to estimate the effect of increasing alarm delays on alarm rates. However, previous systems and methods do not enable estimation of the effect of alarm limits or decreasing alarm delays on alarm rate data, alone.

Moreover, the inventors have recognized that alarm rate data is specific to a particular healthcare ward or other particular healthcare environment, and that statistics available from one ward are likely not directly applicable to another and that statistics from one medical facility are likewise not directly applicable to another. Namely, alarm statistics differ significantly from one healthcare environment to another, and thus utilization of the statistics without accounting for the error will generate erroneous results and lead to improper conclusions and decisions, in this case erroneous estimation of the effect of changing alarm limits or alarm delays on alarm rates. These differences between healthcare environments can be attributed to differences in patient populations—e.g. differences between cardiac wards and respiratory wards, patients of different demographics, age compositions, etc.—as well as differences in work flows, clinical criteria (such as how aggressively medication or certain treatments are used), etc. Thus, the inventors have recognized that patient monitoring data and alarm rate data from one healthcare environment, such as a particular ward (e.g., cardiac ward, neurological ward, neonatal ward) of a healthcare facility, cannot be applied directly to assess alarms in another healthcare environment.

Upon recognition of the foregoing problems and challenges in the relevant field, the inventors developed the disclosed system, device, and method whereby an alarm rate transform is generated enabling an alarm rate model to be accurately applied to predict physiological alarm frequency in different healthcare environments from where the model was generated. For example, an alarm rate model is determined based on patient monitoring data from multiple patients in at least a first healthcare environment, wherein the alarm rate model provides alarm rates at a range of alarm configurations. That alarm rate model can then be applied to other healthcare environments utilizing an alarm rate transform, as described herein.

Initial alarm rate data is collected at a second healthcare environment, for example, wherein the alarm rate data is collected in the second healthcare environment and includes at least one alarm rate and at least one known alarm configuration that is within the range of alarm configurations covered by the alarm rate model. The alarm rate transform is then calculated for the second healthcare environment that compares the initial alarm rate data for the second healthcare environment to the alarm rate model. Thereby, alarm rates at a range of alarm configurations can be estimated for the second healthcare environment without having to collect extensive physiological data from patients and/or extensive alarm rate data at the full range of alarm rate configurations.

The alarm rate transform is utilized to predict alarm rates for the second healthcare environment at different alarm configurations than the known alarm configuration at which the initial alarm rate data for the second healthcare environment was collected. Thereby, alarm rates can be predicted for the patient monitors in the second health care environment using only that initial alarm rate data. For example, predicted alarm rates may be generated for different alarm delay values and different alarm limit values.

FIG. 1 depicts one embodiment of a system for predicting physiological alarm frequency by patient monitoring devices 16. The figure schematically depicts a first healthcare environment 5a at a first healthcare facility 18a. Multiple patients 3a-3c are each connected to patient monitoring systems 16a-16c, which may each include multiple patient monitors collecting different physiological data from the respective patient 3a-3c. Thus, each patient monitoring system 16a-16c may include one or more patient monitors collecting and/or assessing physiological data from the respective patient 3a-3c. Examples of patient monitors include, but are not limited to, an electrocardiograph (ECG), a non-invasive blood pressure monitor (NIBP), an invasive blood pressure monitor, an $SpO_2$ monitor, an electroencephalograph (EEG) a respiration monitor, or any other device or system capable of collecting physiological data or other patient monitoring data. As is common, multiple patient monitors may be connected to each patient 3a-3c, which may be all integrated into a single patient monitoring system 16a-16c or may be separate patient monitors that act individually and are connected to the patient. In either embodiment, the patient monitoring data, i.e. the physiological information collected about the patient, is transmitted on a local network to one more local servers. For example, the patient monitoring data may be managed by a centralized patient monitoring system for the environment and/or healthcare facility and/or may be stored in the patient's medical record. In a distributed or cloud-based implementation, a communication gateway 22a may communicatively connect the local server 20a to a centralized computing system that handles patient monitoring, such as a cloud-based system. For example, the physiological monitoring data may be communicated from the patient monitoring systems 16a-16c to the server 20a or the healthcare facility via any of various communication protocols and/or architectures, such as a network bus (e.g., an Ethernet backbone), a hospital WLAN, or the like.

An alarm rate model is then generated based on the patient monitoring data from the first environment 5a. In certain examples, the alarm statistics may be generated based on multiple environments in the same healthcare facility 18a, or the parameter statistics may be environment-specific such that each ward, or area, of the healthcare facility 18a has its own model-type. For example, the alarm rate model provides alarm rates at a range of alarm configurations determined based on parameter statistics from the first healthcare environment, such as a healthcare ward or group of healthcare wards. The patient monitoring data and parameter statistics are thorough such that a sufficient range of alarm configurations can be reliably determined. For example, several months of patient monitoring data may be collected in a controlled way in order to generate a thorough set of patient monitoring data from the first healthcare environment or group of environments. From that data, the alarm rate model is generated. For example, the alarm rate model may include or describe alarm rates at a range of alarm delay values and a range of alarm limit values.

An alarm rate model is generated for each physiological parameter being predicted. Moreover, an alarm rate model may be generated for each of high and low alarm limits, or thresholds. Thus, for a single monitor parameter, such as $SpO_2$ or respiration rate, an alarm model may be generated modeling a range of low alarm limits and a range of alarm delay values, or may model a range of high alarm limit values and a range of alarm delay values. The alarm delay range for the high alarm limit values may be the same or different than the alarm delay range for the low alarm limit values. Thus, the low limit alarm rate model may describe alarm rates at a range of low alarm limit values and a first range of delay values, and the high limit alarm rate model may describe alarm rates at the range of high alarm limit values and a second range of delay values, wherein the first range of delay values and the second range of delay values are different.

FIGS. 2A and 2B provide exemplary alarm rate models 50 showing alarm rates for a pulse rate monitor at a range of low alarm limits and a range of alarm delays. Thus, where the low alarm limit is 50 and the alarm delay is zero seconds, the alarm rate model 50 indicates an alarm rate of 31.7 alarms per day. Likewise, where the low alarm limit for the pulse rate monitor is 40 and the alarm delay is 90 seconds, the alarm rate is 0.2 alarms per day.

FIG. 2B depicts another exemplary alarm rate model for a pulse rate monitor based on low alarm limits and alarm delays. In this second example, alarm rates and alarm durations are shown for each of the range of low alarm limits and the range of alarm delays. Thus, for each alarm rate, a corresponding average alarm duration is also shown. This can be another piece of data utilized to provide the alarm rate model and utilized as part of the alarm rate transform. Thus, in this embodiment, the average alarm duration is utilized to supplement the alarm rate data and provide additional information that can be used to fit, or customize, the alarm rate model to a particular healthcare environment. In the example, the alarm rate for the pulse rate monitor when the low alarm limit is 50 and the alarm delay is zero seconds is again 31.7 and the alarm duration is three minutes. When the alarm delay is increased to 15 seconds, the alarm rate goes down to 15.8 and the average duration goes down to 2.7 minutes. It can be assumed that both the alarm rate and the alarm duration continue to decrease as the alarm delay increases. Similarly, the alarm rate and the alarm duration decrease as the low alarm limit value decreases and thus the threshold for generating an alarm gets further from the normal, healthy pulse rate value. For visual simplicity, dashes are used to represent the existence of numbers and only an exemplary subset of the values in the table at FIG. 2B are shown. For purposes of the example, it can be assumed that the table at FIG. 2B generally includes the same alarm rate information as shown at FIG. 2A, adding alarm durations for each alarm configuration of alarm delay and low alarm limit.

In another embodiment, the alarm rate model may describe alarm rates at a range of alarm configurations in relative terms, such as a function or formula describing the change in alarm rate values over the range, or span, of alarm configuration. The model can be specific to one configuration (e.g., delay of pulse rate low alarm), or a combination of configurations for one alarm (e.g., delay and limit of pulse rate low alarm), or may be a combination of configurations for several related alarms (e.g., delay and limit of pulse rate low and high alarms).

As described above, the inventors have recognized that each healthcare facility and each environment within each healthcare facility has a unique set of influencing factors on alarm rates, and thus the alarm rate model developed based on physiological data and/or alarm statistics from a first healthcare environment (e.g. 5a) cannot be directly applied to a second healthcare environment (e.g. 5b). Thus, the inventors developed the methods and systems herein that calculate an alarm rate transform that enables application of the alarm rate model to a new environment (e.g. 5b) even though the model is not based on the physiological data or other alarm statistics from that new healthcare environment. Accordingly, the alarm rate model 50 is calibrated as described herein in order to apply the model to predict physiological alarms in a different healthcare environment, such as a different type of healthcare ward and/or a ward at a different healthcare facility. Referring again to FIG. 1, a second healthcare facility 18b has a second healthcare environment 5b where different patients 3d-3f are being monitored by different physiological monitors and monitoring systems 16d-16f.

For each environment to which the alarm rate model 50 will be applied, initial alarm rate data is collected. Thus, in order to apply the alarm rate model generated based on patient monitoring data and/or alarm statistics from the first environment 5a, initial alarm rate data is collected for the second healthcare environment 5b. The initial alarm rate data includes an alarm rate at at least one known alarm configuration that is within the range of alarm configurations described in the alarm rate model. In certain embodiments, the alarm rate data may include alarm rates at at least two known alarm configurations within the range of alarm configurations described in the alarm rate model, which can result in a better and more accurate alarm rate transform. Additionally, in certain embodiments, the initial alarm rate data may further include alarm durations or their average, and the durations can be utilized as another factor of comparison between the initial alarm rate data and the alarm rate model in order to generate a more accurate alarm rate transform. The initial alarm rate data may be collected and stored, for example, on a server computer 20b within the network of the healthcare facility. Alternatively or additionally, the initial alarm rate data may be stored elsewhere and/or transferred to any competing system, such as via the communications gateway 22b, which may communicatively connect the local server 20b or other computing device storing the initial alarm rate data to a computing system assessing the alarm rate transform and/or the alarm rate model.

Referring still to FIG. 2, a computing system 200 may be configured for executing the method of predicting physiological alarm frequency for one or more patient monitors, such as at the second healthcare environment 5b. The computing system 200 generally comprises a processing system 202 and a storage system 204. The computing system 200 stores software configured for execution of the method of predicting the physiological alarm frequency, herein referred to as an alarm predictor module 206. The alarm predictor module is stored in the storage system 204 and comprises computer executable instructions configured to predict physiological alarm frequencies by patient monitors at different configurations. The storage system 204 may include any number of one or more storage devices, which may include memory, a hard disc drive, or other form of non-volatile memory or volatile memory The computing system 200 may be configured to receive the alarm rate model 50 and the initial alarm rate data for the second healthcare environment and to generate an alarm rate transform thereon. The alarm rate model can thus be calibrated for the second healthcare environment and can then be utilized to predict alarm rates for different alarm delay values and alarm limit values, as well as any other alarm optimization values, or patient monitors in the second healthcare environment 5b. In certain embodiments, the computing system 200 may be connected with and/or comprised part of the computer network at the second healthcare facility 18b or may be a stand-alone system that receives information, including the alarm rate model and/or the initial alarm rate data gathered and stored at the first and second healthcare facilities 18a and 18b.

Figures 3, 4:
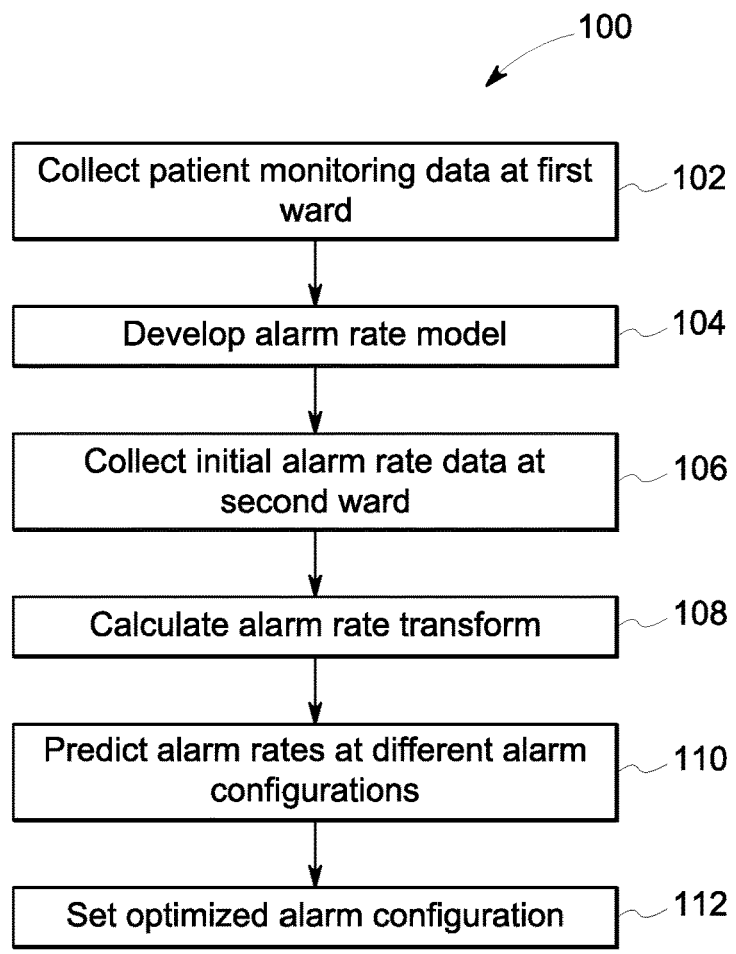
FIG. 3 depicts exemplary alarm rate data collected from a second healthcare environment using known configurations.
FIGS. 4 and 5 depict exemplary methods of predicting physiological alarm frequency by patient monitors.

FIG. 3 depicts one embodiment of exemplary initial alarm rate data 60 for a second healthcare environment 5b. The initial alarm rate data 60 includes alarm rates at two known alarm configurations, which include two different combinations of low alarm limit values and alarm delay values that are all within the range of alarm configurations described by the alarm rate model 50. In the example in FIG. 3, alarm durations are also included. The alarm rate transform is then generated by comparing the initial alarm rate data 60 from the second healthcare environment to the appropriate alarm rate model 50, such as that shown in FIG. 2B. The resulting alarm rate transform calibrates the alarm rate model 50 to the initial alarm rate data 60 for the second healthcare environment 5b so as to produce about the same alarm rate at each of the known alarm configurations represented in the initial alarm rate data. Thus, with respect to the example at FIG. 3, the alarm rate transform represents an adjustment to the alarm rate model 50 so that the alarm rate and alarm duration at each of the known alarm configurations, including a low alarm limit of 44 with an alarm delay of fifteen seconds and a low alarm limit of 46 with an alarm delay of thirty seconds. The remainder of the values in the range can be estimated based on the differences between the few values in the initial alarm rate data 60 and the corresponding values in the model. For example, the rest of the table in FIG. 3 can be filled out using the alarm model 50 adjusting each of the values based on the transform defined by the differences between the alarm rate model value and the values in the initial alarm rate data at those known alarm configurations. Additionally, if duration of each alarm event is available, this information can be directly used to deduce the effect of additional delay for the alarm rates, as any alarm shorter than the added delay would not be generated.

FIG. 4 depicts one embodiment of the method 100 of predicting physiological alarm frequency by patient monitors. Patient monitoring data is collected at a first environment at step 102. An alarm rate model has been generated at step 104 based on the collected patient monitoring data. For example, various alarm limits, or alarm detection thresholds, and/or alarm notification delay times may be simulated using the patient monitoring data in order to generate an environment-based alarm rate model that represents an efficiently wide range of alarm configurations. Initial alarm rate data is then collected at a different healthcare environment, such as a different healthcare ward, at step 106. Steps are then executed to calibrate the alarm rate model for use in predicting the alarms of the second healthcare environment. For example, such steps must be executed by the alarm predictor module 206 stored and executed by the computing system 200. Namely, the alarm rate transform is calculated at step 108. Alarm rates are then predicted at different alarm configurations using the calibrated alarm rate model, which is calibrated via the alarm rate transform, as represented at step 110. The predicted alarm rates can be used to select alarm configurations that produce sufficiently low alarm rate considering the workflow hospital.

Figure 5:
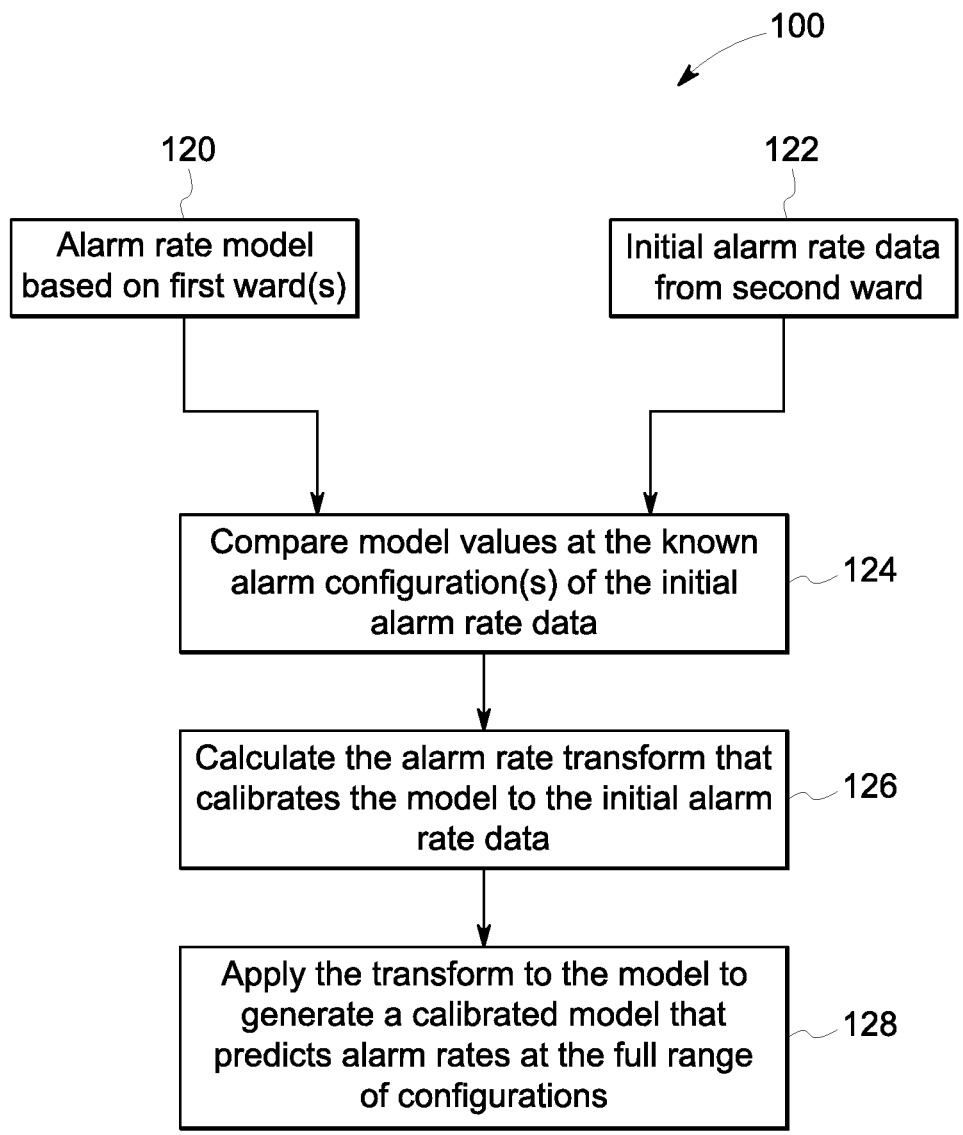

FIG. 5 represents further steps in the method 100 of predicting physiological alarm frequency. In particular, the steps at FIG. 5 represent one embodiment of calculating an alarm rate transform. The alarm rate model, which as described above is based on physiological data of multiple patients collected at at least a first healthcare environment, is provided at step 120. Initial alarm rate data from a second healthcare environment is provided at step 122, which as described above, includes at least one alarm rate at at least one known alarm configuration. The model value at the one or more known alarm configurations represented in the initial alarm rate data shown in FIG. 3 are compared to the corresponding values in the alarm rate model 50 table shown at FIG. 2B. An alarm rate transform is then determined at step 126 that calibrates the alarm rate model to the initial alarm rate data. The alarm rate transform is then applied to the model in order to generate a calibrated model that can be used to set alarm configuration values in the relevant patient monitors—i.e. those patient monitors assessing the physiological parameter represented in the model. The calibrated model describes alarm rates at the full range of configurations represented by the alarm rate model and provides an accurate prediction of alarm rates even though the initial alarm rate data only represented a few known alarm configurations. Thereby, alarm prediction can be accurately carried out within each healthcare environment without having to generate exhaustive patient monitoring data in order to develop an accurate model.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A method of predicting physiological alarm frequency by patient monitors, the method comprising:
   collecting patient monitoring data of multiple patients in at least a first healthcare environment;
   determining an alarm rate model based on the patient monitoring data, wherein the alarm rate model describes alarm rates at a range of alarm configurations;
   collecting initial alarm rate data for a second healthcare environment, wherein the initial alarm rate data includes at least one alarm rate at at least one known alarm configuration within the range of alarm configurations;
   calculating an alarm rate transform for the second healthcare environment comparing the initial alarm rate data for the second healthcare environment to the alarm rate model; and
   predicting alarm rates for the second healthcare environment at a different alarm configuration than the at least one known alarm configuration of the initial alarm rate data by applying the alarm rate transform to the alarm rate model.

2. The method of claim 1, wherein the alarm rate transform calibrates the alarm rate model to the initial alarm rate data for the second healthcare environment so as to produce an alarm rate at each of the at least one known alarm configuration that estimates the initial alarm rate data for the second healthcare environment.

3. The method of claim 1, wherein the initial alarm rate data includes alarm rates at at least two known alarm configurations within the range of alarm configurations.

4. The method of claim 1, wherein the range of alarm configurations for the alarm rate model include a range of alarm delay values and a range of alarm limit values.

5. The method of claim 4, wherein the healthcare environment is a ward of a hospital, and wherein a low limit alarm rate model and a high limit alarm rate model are provided for each physiological parameter monitored by the patient monitor, wherein the low limit alarm rate model describes alarm rates at a range of low alarm limit values for the physiological parameter and the high limit alarm rate model describes alarm rates at a range of high alarm limit values for the physiological parameter.

6. The method of claim 5, wherein the low limit alarm rate model describes alarm rates at the range of low alarm limit values and a first range of delay values, and the high limit alarm rate model describes alarm rates at the range of high alarm limit values and a second range of delay values, wherein the first range of delay values and the second range of delay values are different.

7. The method of claim 4, wherein the initial alarm rate data includes the at least one alarm rate at a known alarm delay value that is within the range of alarm delay values and at a known alarm limit value that is within the range of alarm limit values.

8. The method of claim 7, wherein the initial alarm rate data includes an alarm rate at each of at least two known alarm delay values that are within the range of alarm delay values and/or at each of at least two known alarm limit values that are within the range of alarm limit values.

9. The method of claim 7, wherein the alarm rate model further includes alarm durations at the range of alarm delay values and the range of alarm limit values, and the initial alarm rate data further includes an alarm duration for each known alarm configuration.

10. The method of claim 9, wherein the alarm rate transform calibrates the alarm rate model to the initial alarm rate data for the second healthcare ward so as to further produce an alarm duration at the at least one known alarm configuration that estimates the initial alarm rate data for the second healthcare ward.

11. A system for predicting physiological alarm frequency by patient monitors, the system comprising:
    an alarm rate model stored on a memory, wherein the alarm rate model describes alarm rates at a range of alarm configurations and is based on patient monitoring data from multiple patients in at least a first healthcare environment;
    a plurality of patient monitors configured to collect patient monitoring data from patients in a second healthcare environment;
    a processor configured to:
    receive initial alarm rate data for a second healthcare environment, wherein the initial alarm rate data is based on the patient monitoring data and includes at least one alarm rate at at least one known alarm configuration within the range of alarm configurations;
    calculate an alarm rate transform for the second healthcare environment comparing the initial alarm rate data for the second healthcare environment to the alarm rate model; and
    predict alarm rates for the second healthcare environment at a different alarm configuration than the at least one known alarm configuration of the initial alarm rate data based on the alarm rate transform.

12. The system of claim 11, wherein the alarm rate transform calibrates the alarm rate model to the initial alarm rate data for the second healthcare environment so as to produce an alarm rate at each of the at least one known alarm configuration that estimates the initial alarm rate data for the second healthcare environment.

13. The system of claim 11, wherein the alarm rate model includes alarm rates at a range of alarm delay values and a range of alarm limit values.

14. The system of claim 13, wherein the alarm rate model further includes alarm durations at the range of alarm delay values and the range of alarm limit values, and the initial alarm rate data further includes an alarm duration for each known alarm configuration.

15. The system of claim 11, wherein the initial alarm rate data includes alarm rates at at least two known alarm configurations within the range of alarm configurations.

16. A non-transitory computer readable medium configured for predicting physiological alarm frequency by patient monitors, the non-transitory computer readable medium containing program instructions that cause the computer to perform steps comprising:
    receiving an alarm rate model based on patient monitoring data from a first healthcare environment, wherein the alarm rate model describes alarm rates at a range of alarm configurations;
    receiving initial alarm rate data based on patient monitoring data from a second healthcare environment, wherein the initial alarm rate data includes at least one alarm rate at at least one known alarm configuration within the range of alarm configurations;

comparing the initial alarm rate data for the second healthcare environment to the alarm rate model;

calculating an alarm rate transform for the second healthcare environment based on the comparison; and predicting alarm rates for the second healthcare environment at a different alarm configuration than the at least one known alarm configuration of the initial alarm rate data based on the alarm rate transform.

17. The non-transitory computer readable medium of claim 16, wherein the alarm rate transform calibrates the alarm rate model to the initial alarm rate data for the second healthcare environment so as to produce an alarm rate at each of the at least one known alarm configuration that estimates the initial alarm rate data for the second healthcare environment.

18. The non-transitory computer readable medium of claim 16, wherein the range of alarm configurations for the alarm rate model include a range of alarm delay values and a range of alarm limit values;

wherein the alarm rate model includes alarm rates at a range of alarm delay values and a range of alarm limit values.

19. The non-transitory computer readable medium of claim 18, wherein the initial alarm rate data includes an alarm rate at each of at least two known alarm delay values that are within the range of alarm delay values and/or at each of at least two known alarm limit values that are within the range of alarm limit values;

wherein the alarm rate model further includes alarm durations at the range of alarm delay values and the range of alarm limit values, and the initial alarm rate data further includes an alarm duration for each known alarm configuration.

20. The non-transitory computer readable medium of claim 19, wherein the alarm rate transform calibrates the alarm rate model to the initial alarm rate data for the second healthcare environment so as to further produce an alarm duration at the at least one known alarm configuration that estimates the initial alarm rate data for the second healthcare environment.

* * * * *